United States Patent [19]

Bille

[11] Patent Number: 5,062,702

[45] Date of Patent: Nov. 5, 1991

[54] DEVICE FOR MAPPING CORNEAL TOPOGRAPHY

[75] Inventor: Josef F. Bille, Rancho Santa Fe, Calif.

[73] Assignee: Intelligent Surgical Lasers, Inc., San Diego, Calif.

[21] Appl. No.: 494,683

[22] Filed: Mar. 16, 1990

[51] Int. Cl.$^5$ .............................................. A61B 3/10
[52] U.S. Cl. ..................................... 351/212; 351/221
[58] Field of Search ........................ 351/206, 212, 221; 356/376

[56] References Cited

PUBLICATIONS

Ronald Cubalchini, Modal Wave-Front Estimation from Phase Derivative Measurements.
W. H. Southwell, Wave-Front Estimation from Wave-Front Slope Measurements, Optical Society of America, vol. 70, No. 8, Aug. 1980, pp. 998–1005.
H. C. Howland, Objective Technique for the Determination of Monochromatic Aberrations of the Human Eye, Optical Society of America, vol. 1, No. 9, Sep. 1984, pp. 987–992.
Klaus R. Freischlad and Chris L. Koliopoulos, Modal Estimation of a Wave Front from Difference Measurements Using the Discrete Fourier Transform, Optical Society of America, vol. 3, No. 11, Nov. 1986, pp. 1852–1861.
Stephen D. Klyce and Steven E. Wilson, Imaging, Reconstruction, and Display of Corneal Topography, New Methods in Microscopy and Low Light Imaging, vol. 1161, 1989, pp. 409–416.
J. F. Bille, B. Grimm, J. Liang, K. Mueller, Imaging of the Retina by Scanning Laser Tomography New Methods in Microscopy and Low Light Imaging, vol. 1161, 1989, pp. 417–425.
Phillip C. Baker, Holographic Contour Analysis of the Cornea, New Methods in Microscopy and Low Light Imaging, vol. 1161, 1989, pp. 426–437.
Modal Wave-Front Estimation from Phase Derivative Measurements.

Primary Examiner—Paul M. Dzierzynski
Attorney, Agent, or Firm—Nydegger Associates

[57] ABSTRACT

A device for mapping the topography of the cornea of an eye has a light source for directing a beam of collimated monochromatic light characterized by a flat wave front onto the cornea. Positioned between the light source and the cornea is an objective lens for focusing this flat wave front toward the cornea as a converging spherical wave front. The light reflected from the cornea passes back through the objective lens to establish a reflected wave front having deviations from the flat wave front caused by aberrations on the cornea that are indicative of corneal topography. This reflected wave front is then segmentally focused by a lens array into a pattern which reveals the deviations for use in mapping the topography of the cornea.

5 Claims, 2 Drawing Sheets

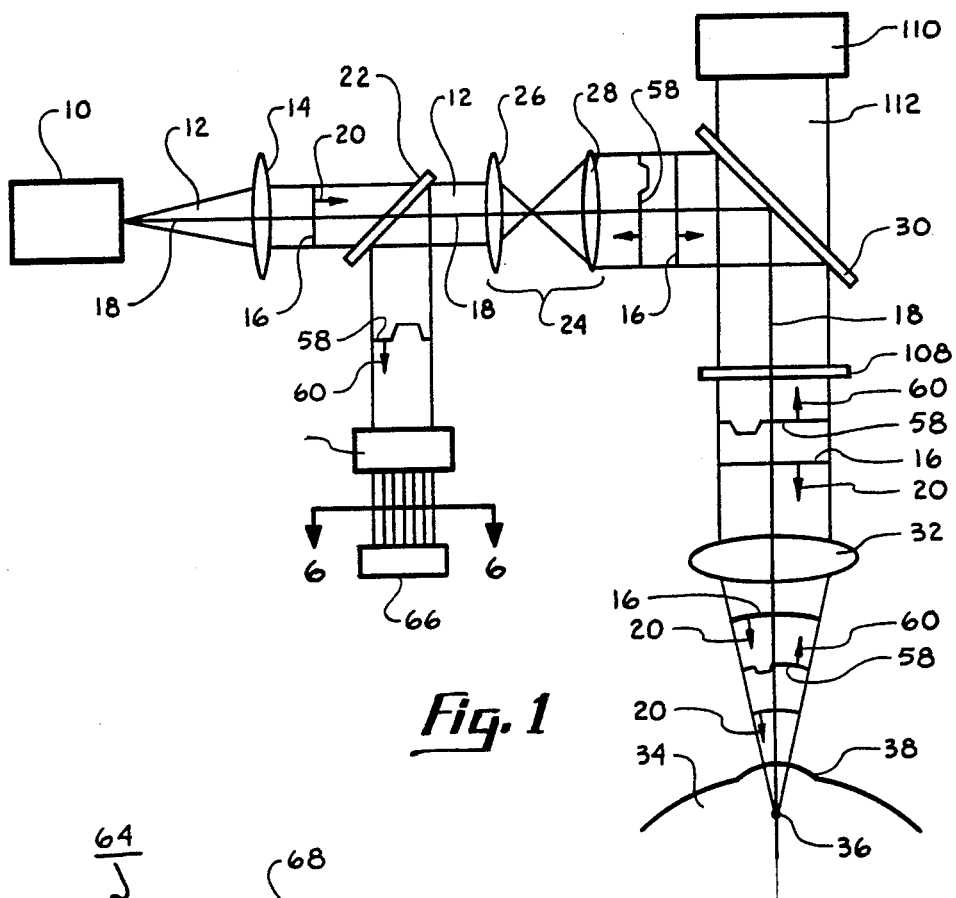
Fig. 1
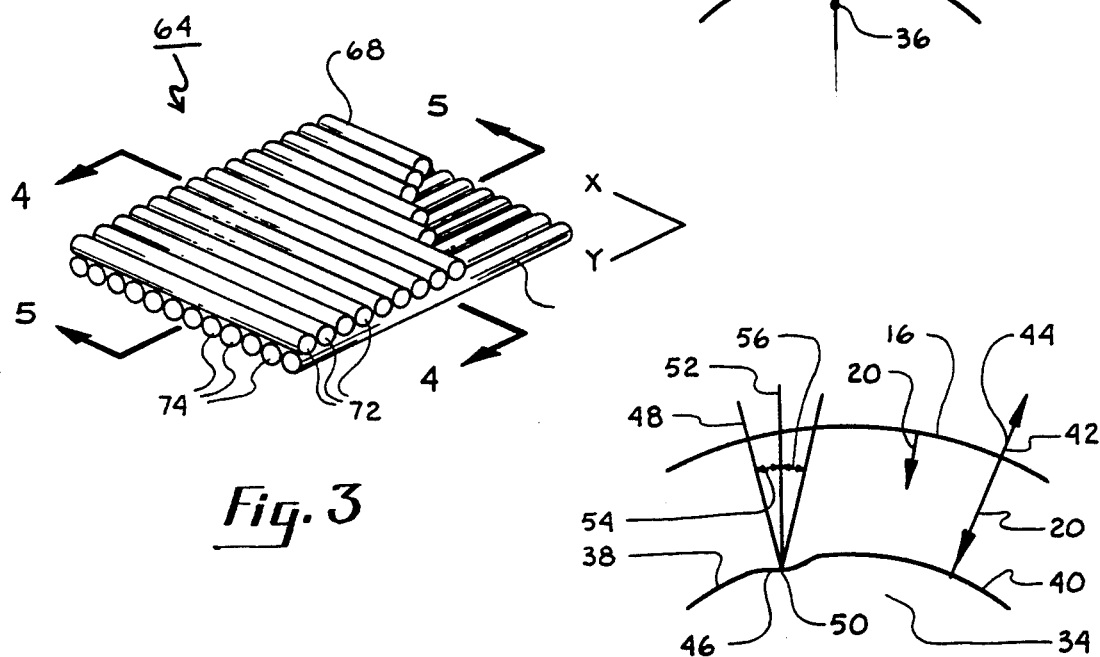
Fig. 3
Fig. 2

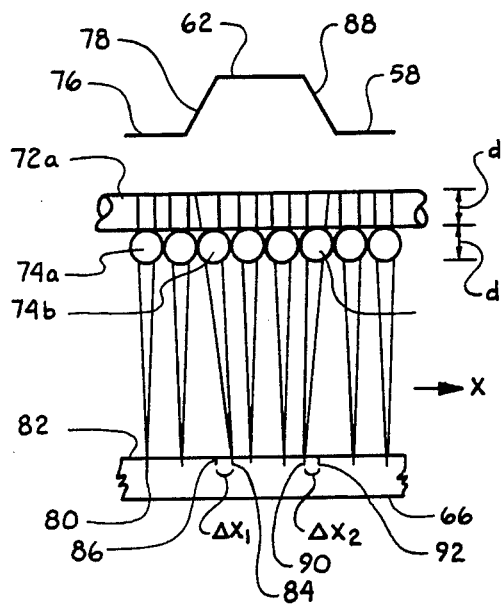
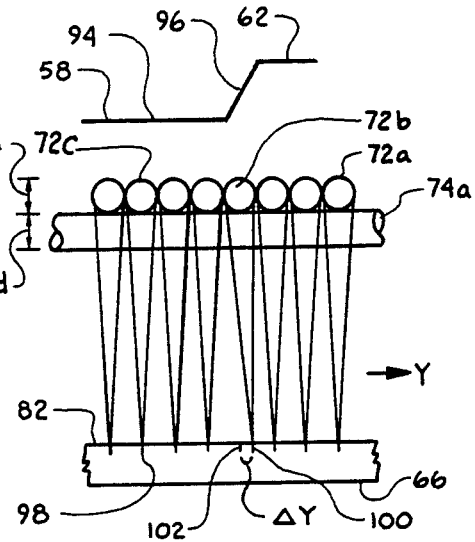
Fig. 4    Fig. 5
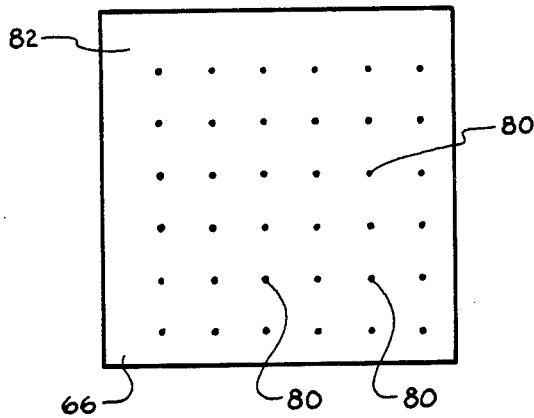
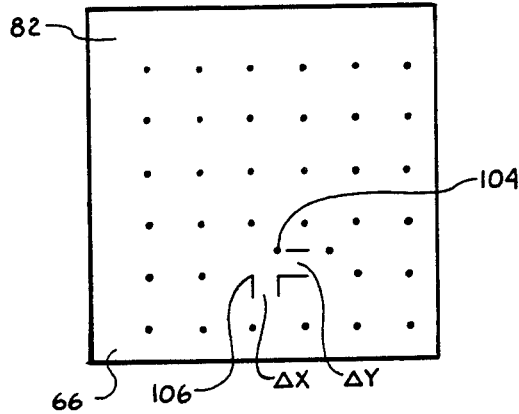
Fig. 6A    Fig. 6B

DEVICE FOR MAPPING CORNEAL TOPOGRAPHY

FIELD OF THE INVENTION

The present invention pertains generally to ophthalmic instruments. More particularly, the present invention pertains to ophthalmic instruments which measure and determine the corneal topography of a human eye. The present invention is particularly, but not exclusively, useful for homogeneously mapping the topography of the entire cornea of the eye with equal precision and uniform accuracy.

BACKGROUND OF THE INVENTION

Due to the enchanced precision with which ophthalmic surgery can now be performed using laser instruments, it is increasingly important that corneal topography be determined with an accuracy which will allow full exploitation of the capabilities and potential of these instruments. Further, it is important and desirable that the entire anterior surface area of the cornea, and not just a part thereof, be accurately mapped in order for laser instruments to be employed most efficaciously. To this end, several devices have been proposed.

One type of instrument which is now used to measure the anterior surface of the cornea relies on the use of Placido disc illumination. In accordance with the technique used by such an instrument, a template having a series of expanding planar concentric circles, or rings, is positioned in front of the eye and the light reflected from the cornea through the template is analyzed. Specifically, the distortion of light reflected through the ring pattern by the conditions that exist on the corneal surface is analyzed to help determine the corneal topography. As can be expected, the efficacy of this technique is dependent on the precise geometric placement of the ring pattern with respect to the corneal reflections. Importantly, however, the accuracy of this technique is greatly diminished, indeed obviated, as the diameter of the ring is diminished. Unfortunately, this occurs in the center of the template which receives light reflected from the center of the cornea. Thus, the diminution in accuracy accurs at the very part of the cornea where the greatest accuracy is required.

Another type of device for analyzing a corneal contour employs a modal wave front estimation from phase derivative measurements. An example of such a device is disclosed and discussed in an article written by Philip C. Baker entitled "Holographic Contour Analysis of the Cornea" which appeared in SPIE Vol 1161 (1989). In the operation of this device, a wave front reflected from the corneal surface is detected and analyzed to determine phase change interferences which result from perturbations on the surface. An interference fringe pattern is thus created with data which can be digitized for evaluation. There are, however, some disadvantages with such a device. For example, the return signal is extremely noisy. Thus, there is a high probability for random reconstruction error. Further, the technique involves numerical complexities and an inherent problem for determining compatible polynomials. Still further, and perhaps most importantly, phase derivative measurements require analysis of an unperturbed reflected wave front. Stated differently, the signal to be analyzed is spread over the whole wave front. Consequently, in order to obtain a signal which will yield a fringe pattern with sufficient information to be meaningfully analyzed, the light source used must provide a relatively high intensity input, i.e. a flash of light. This, at best, can be uncomfortable for the patient.

In light of the above, an object of the present invention is to provide a device for mapping the topography of the eye which provides a uniform homogeneous mapping of the entire corneal surface of most significant interest. Another object of the present invention is to provide a device for mapping the topography of the eye which is equally accurate for all portions of the anterior surface of the cornea which are of significant interest. Still another object of the present invention is to provide a device for mapping the topography of the eye which gives information that can be beneficially used for a wide variety of ophthalmic procedures. Yet another object of the present invention is to provide a device for mapping the topography of the eye which is relatively easy to use and comparatively cost-effective.

SUMMARY OF THE INVENTION

The preferred embodiment of the device for mapping the topography of the cornea of the eye includes a light source for generating a beam of collimated monochromatic light. As intended for the present invention, the beam of light from the light source is characterized by a directed wave front having a predetermined curvature. Preferably, this predetermined curvature is such that the directed wave front is flat. An objective lens is positioned on the optical axis which extends from the light source to the surface of the cornea and this lens is used to focus the directed wave front toward the surface of the cornea. As so focused by the objective lens, the beam of light travels toward the cornea with a converging spherical wave front.

Light in the beam that is reflected from the surface of the cornea passes back substantially along the optical axis and through the objective lens. After reflection from the cornea, the reflected light establishes a reflected wave front which differs from the initially directed wave front by deviations which are indicative of corneal topography. A beam splitter is positioned on the optical axis between the light source and the objective lens for directing the reflected wave front toward a detector The device of the present invention has a detector which includes a lens array for separately focusing segments of the reflected wave front, and a charge-coupled device for determining the location of the focal points of the focused segments. More specifically, the lens array comprises a first lens layer having a plurality of juxtaposed cylindrical lenses which are positioned adjacent a second lens layer having a plurality of juxtaposed cylindrical lenses. As positioned, the longitudinal axes of the lenses of the first layer are substantially perpendicular to the longitudinal axes of the lenses of the second layer. Consequently, the light characterized by the reflected wave which is incident on the lens array is concentrated by separately focusing segments of the reflected wave which are substantially defined by the diameters of the cylindrical lenses. These individually focused segments of the reflected wave front are then incident on the charge-coupled device and the location of incidence of their focal points on the charge-coupled device is used in mapping the corneal topography.

In the operation of the device for mapping the cornea of the eye, it is to be understood that the detector would focus segments of a light beam having a flat wave front into a grid or pattern of aligned focal points. Thus, if the area of the cornea being mapped is perfectly spherical, the reflected wave front will be flat and this aligned grid pattern will result. On the other hand, a reflected wave front passing through the lens array, which is not a flat wave front, will have deviations that cause movement or misalignment of the segment focal points. The charge-coupled device is used to determine the actual pattern of segment points, including misalignments, and present this pattern for use in subsequent calculations to map the corneal topography.

In an alternate embodiment of the present invention, the beam splitter is replaced by a polarized beam splitter and a quarter wave plate is added. Specifically, monochromatic polarized light is directed along the optical axis through the polarized beam splitter and is then rotated by the quarter wave plate enroute to the cornea. The light reflected from the cornea is then again rotated by the quarter wave plate to be polarized perpendicular to the incoming wave, and is subsequently diverted off the optical axis and toward the detector by the polarized beam splitter.

For purposes of the present invention, the light source is preferably a combination of a laser diode and a collimating lens. The light source may, however, be a combination of a collimating lens and an incandescent light source with a spectral filter which is positioned relative to the incandescent source to pass monochromatic light toward the cornea.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 2 is a cross-sectional schematic showing incident and reflected light relative to the cornea of an eye;

FIG. 3 is a perspective view of the lens array of the present invention with portions broken away for clarity;

FIG. 4 is a cross-sectional view of a portion of the lens array as seen along the line 4—4 in FIG. 3 in its relationship to both an input reflected wave front and a charge-coupled device;

FIG. 5 is a cross-sectional view of a portion of the lens array as seen along the line 5—5 in FIG. 3 in its relationship to both an input reflected wave front and a charge-coupled device;

FIG. 6A is a grid pattern of segment focal points as detected by the device of the present invention that is indicative of a perfectly spherical cornea; and FIG. 6B is a grid pattern of segment focal points as detected by the device of the present invention that is indicative of an aberration on the cornea.

DESCRIPTION OF THE PREFERRED EMBODIMENT

Figure 1:
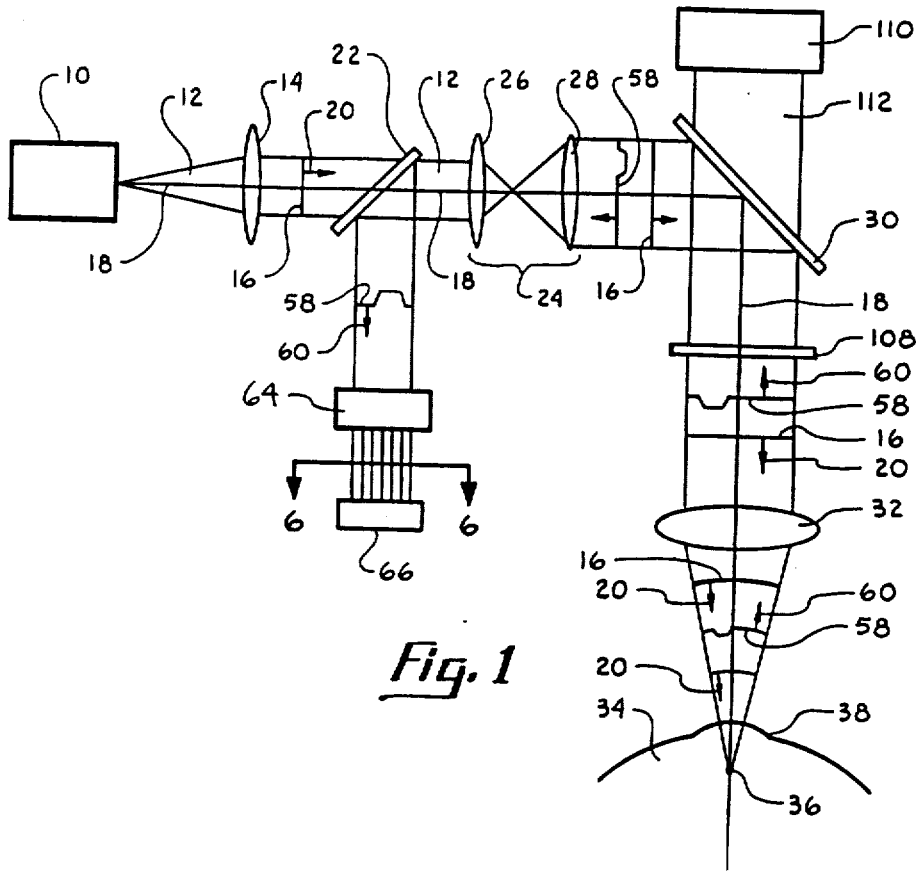
FIG. 1 is a schematic diagram of the interactive components of the device of the present invention shown in relation to the eye and cornea of a patient.

Referring initially to FIG. 1, it will be seen that the device for mapping corneal topography according to the present invention includes a light source 10. Importantly, light source 10 generates a beam 12 of monochromatic light which is collimated by a collimating lens 14. Preferably, light source 10 is a laser diode of any type well known in the pertinent art. For example, a laser diode which emits light having a 820 nm wavelength is suitable for the present invention. Light source 10 may, however, be an incandescent lamp having a spectral filter. In either case, it is necessary that light source 10, in combination with collimating lens 14, generates a coherent beam 12 of monochromatic light.

As will be appreciated by the skilled artisan, the beam 12 of collimated monochromatic light that is generated by light source 10 will be characterized by a directed wave front 16 which is flat and which travels along the optical axis 18 of the device in a direction indicated by the arrow 20. Although the predetermined curvature for directed wave front 16 is preferably flat, modifications of the device are possible to accommodate directed wave fronts 16 having a different predetermined curvature. It is important, however, that directed wave front 16 have a predetermined curvature.

A 50/50 beam splitter 22, of any type well known in the pertinent art, is positioned on optical axis 18 to pass beam 12 toward a telescopic unit 24. As shown in FIG. 1, telescopic unit 24 includes a pair of lenses 26, 28 which are optically arranged in a well known configuration to expand beam 12 as it progresses along optical axis 18 in the direction of arrow 20. Another 50/50 beam splitter 30 is positioned on optical axis 18 to divert the beam 12, and consequently directed wave front 16, toward an objective lens 32.

In accordance with the present invention, objective lens 32 is positioned relative to the eye 34 to focus the beam 12 onto the center of curvature 36 of the cornea 38. Thus, the directed wave 16 emerges from objective lens 32 and travels toward the center of curvature 36 of cornea 38 as a converging spherical wave front. As an order of magnitude, the radius of curvature (i.e. the distance from the center of curvature 36 to the anterior surface of cornea 38) will be approximately seven and eight tenths millimeters (7.8 mm). It is a substantially accurate assumption that, for a normal eye 34, the center of the cornea 38 (e.g. a circular area of approximately four millimeters (4 mm) in diameter) is spherical in its contour. Accordingly, for a spherical-shaped cornea 38, all the light rays of wave front 16 will impact cornea 38 simultaneously and be reflected back along the same path.

A more complete appreciation of the optics involved may be had by reference to FIG. 2. With reference to FIG. 2, first consider a surface portion 40 of cornea 38 that is spherically contoured. Because the directed wave front 16 after being focused by objective lens 32 is now also spherical, a light ray 42 in wave front 16 will travel in a direction that is normal to surface portion 40 of cornea 38. Thus, as light ray 42 approaches portion 40 in the direction indicated by arrow 20, it will be reflected back along the same path in the direction of arrow 44. Again, this occurs when the converging spherical wave front 16 is incident on a spherical surface portion 40 of eye 34.

It happens, however, that cornea 38 may be aspherical and have aberrations such as the indentation 46. To understand how an indentation 46 will affect directed wave front 16, consider the light ray 48 of wave front 16 which is incident on cornea 38 in the area of indentation 46. At the point 50 where light ray 48 strikes cornea 38 it will be seen that the direction normal to cornea 38 is represented by the line 52. As is well known to the skilled artisan, the angle of incidence for a light ray, as measured from normal, equals the angle of reflection, as measured from this same normal. Consequently, as light ray 48 of directed wave front 16 strikes point 50 on cornea 38 at an angle of incidence 54, the light ray 48 will be reflected from cornea 38 at an angle of reflection 56 that is equal to the angle of incidence 54. In order to appreciate the orders of magnitude involved, it is known that a six (6) diopter indentation 46 in cornea 38 will cause a light ray 48 to reflect from cornea 38 through an angle of approximately fifteen (15) arc minutes. Thus, in such a case, both the angle of incidence 54 and the angle of reflection 56 will be approximately equal to seven and one half (7.5) arc minutes. In any event, all of the light rays in directed wave front 16, including both the normal and angled rays, are reflected from cornea 38 as a reflected wave front 58.

As shown in FIG. 1, after the directed wave front 16 is incident on cornea 38, it returns as a reflected wave front 58 which travels back along the optical axis 18 in the direction indicated by arrow 60. Further, for purposes of discussion, reflected wave front 58 is shown with a deviation 62 which is indicative of a topographical aberration (e.g. indentation 46) on the anterior surface of cornea 38. More specifically, deviation 62 is shown on the reflected wave front 58 before and after it passes through objective lens 32.

In FIG. 1, it can be seen that the reflected wave front 58 is reflected by beam splitter 30 back through the telescopic unit 24 and is then diverted off optical axis 18 by the beam splitter 22. The diverted reflected wave front 58 is then incident on a detector which includes a lens array 64 and a charge-coupled device (CCD) 66. Specifically, light incident on lens array 64 is concentrated in segments and focused by lens array 64 onto the CCD 66.

FIG. 3 shows that the lens array 64 comprises a first or upper lens layer 68 which is positioned adjacent a second or lower lens layer 70. More specifically, lens layer 68 comprises a plurality of juxtaposed cylindrical lenses 72. Similarly lens layer 70 comprises a plurality of juxtaposed cylindrical lenses 74. As shown, the cylindrical lenses 72 of lens layer 68 are positioned with their respective longitudinal axes aligned in the indicated x-direction. On the other hand, the cylindrical lenses 74 of lens layer 70 are positioned at right angles to the lenses 72 and have their respective longitudinal axes aligned in the indicated y-direction.

The effect lens array 64 has on a reflected wave front 58 can best be seen in FIGS. 4 and 5 where it will be seen that the reflected wave front 58, including deviation 62, is characterized by various combinations of both flat portions 76 and angled portions 78. First consider the flat portion 76 of reflected wave front 58 as shown in FIG. 4. As light rays in this portion 76 pass through the cylindrical lens 72a they converge toward a theoretical focal line (not shown) that is parallel to the longitudinal axis of the lens 72a. They do not, however, converge along the longitudinal axis of the lens 72a. As these same rays then pass through the cylindrical lens 74a they are focused to converge on a focal line (not shown) that is theoretically perpendicular to the focal line of lens 72a. The result of the combined focusing of lenses 72a and 74a is that the light rays in flat portion 76 are focused to a focal point 80 which is at the intersection of the theoretical focal lines and located on surface 82 of CCD 66. In contrast, consider the affect lens array 64 has on the angled portion 78 of reflected wave front 58. While lens 72a still focuses the light to converge on a theoretical focal line that is parallel to the longitudinal axis of lens 72a, by virtue of the inclination of angled portion 78 this light is shifted along the longitudinal axis of the lens 72a. As this light next passes through cylindrical lens 74b it is focused, as before with flat portion 76, onto a theoretical line that is parallel to the longitudinal axis of lens 74b. Again, the result of the combined focusing of lens 72a and 74b is a focal point. In this case, however, the light in angled portion 78 is focused to a focal point 84 that is shifted a distance $\Delta x_1$ from the point 86 where light in angled portion 78 would have been focused had portion 78 been flat.

Under an analysis similar to the one used above for flat portion 76 and angled portion 78, it can be appreciated that the light in angled portion 88 shown in FIG. 4 will be focused by cylindrical lens 72a and cylindrical lens 74c onto a focal point 90 that is a distance $\Delta x_2$ from the point 92 where light in angled portion 88 would have been focused had portion 88 been flat.

The affect lens array 64 has on reflected wave front 58 in the y-direction can be best seen by referring to FIG. 5. Again, as along the x-direction, reflected wave front 58 can be characterized by various combinations of both flat portions 94 and angled portions 96. Using the same analysis as above, the light in flat portion 94 which passes through cylindrical lenses 72c and 74a will be focused to an unshifted focal point. On the other hand, light in angled portion 96 is shifted through a distance $\Delta y$ and focused to the focal point 100 which is at the distance $\Delta y$ from the point 102 where it would otherwise have been focused had portion 96 been flat.

With the above in mind, it is to be appreciated that when each cylindrical lens 72, 74 has a diameter d, the reflected wave front 58 will be effectively divided into contiguous square segments which have sides of length d. As intended for the present invention each of the lens layers 68, 70 respectively comprise eleven (11) cylindrical lenses 72, 74. Further, each cylindrical lens 72, 74 is preferably one (1) mm in diameter (i.e. d equals one (1) mm). Consequently, lens array 64 individually focuses reflected wave front 58 into one hundred twenty-one (121) separate segments which are each one (1) mm square. Thus, the light in reflected wave front 58 is concentrated by lens array 64 in each segment and focused onto surface 82 of CCD 66. For purposes of the present invention, lens array 64 is optically positioned sufficiently near cornea 38 so that the light rays in each segment of reflected wave front 58 were initially in a respectively corresponding segment of directed wave front 16. This will effectively be the case for all light rays, to include even those which are reflected at an angle from cornea 38. This is so because the reflected angle is usually less than fifteen (15) arc minutes when light is reflected from cornea 38 as a result of a corneal aberration such as indentation 46.

FIGS. 6A and 6B are representative of the locations of focal points on surface 82 of CCD 66 that result from the passage of reflected wave front 58 through lens array 64. Specifically, FIG. 6A shows a grid or pattern of aligned focal points 80 which would result if reflected wave front 58 were flat. This would be the case if cornea 38 is spherical. FIG. 6B, on the other hand, illustrates a case where reflected wave front 58 includes deviations due to an indentation 46 on cornea 38. Specifically, FIG. 6B shows a representative focal point 104 which has been moved through the distances $\Delta x$ and $\Delta y$ because of an indentation 46 on cornea 38. Although the deviation 62 discussed herein has used indentation 46 as an example, it is to be appreciated that cornea 38 may have bumps (not shown) as well as indentations on its surface. Whether the surface aberration is a bump or an indentation does not, however, make any difference in the functioning of the device for mapping corneal topography according to the present invention. In either case, the same basic principles of optical physics are employed.

As will be appreciated by the skilled artisan, surface 82 of CCD 66 may comprise a plethora of pixels (not shown) which are responsive to the increased intensity of light at the various focal points on surface 82. With electronic componentry (not shown) these focal points can be oriented in their relationship to each other and the deviations from a predetermined pattern used to map the topography of cornea 38. Further, using appropriate mathematical computations (e.g. Taylor Series) the topographical surface of cornea 38 between the various focal points can be approximated with sufficient accuracy. More specifically, the skilled mathematician will appreciate that, with the proper calculation of appropriate polynomials, an algorithm can be constructed for computation of an approximated surface for cornea 38. Stated differently, and somewhat simplistically, an algorithm can be formulated by one skilled in the pertinent art to convert the information developed by CCD 66 (e.g. the pattern of points 102 as shown in FIG. 6B) into an approximate model of the corneal topography (e.g. the surface portion 40 shown in FIG. 2).

By way of example, FIG. 6A shows an aligned grid of focal points which are representative of a spherical cornea 38. An indentation (e.g. indentation 46) in cornea 38, however, will cause the reflected wave front 58 to create a pattern of focal points such as the one shown in FIG. 6B. If so, the various deviations, $\Delta x$ and $\Delta y$, of each focal point 104 can be used to map corneal topography.

Calibration of the device for mapping corneal topography can be accomplished by initially diverting a directed wave front 16 through lens array 64 without having it reflected by cornea 38. Thus, a base pattern, such as shown in FIG. 6A, can be created with which to compare an actual pattern such as the one shown in FIG. 6B which is reflected from cornea 38.

In an alternative embodiment of the device for mapping the topography of the cornea, as stated above, the light source 10 may be an incandescent light rather than a laser diode. If an incandescent light is used, however, a spectral filter will be required to establish a beam 12 of monochromatic light. In either event, a collimating lens 14 must be employed to ensure that the light rays in beam 12 are collimated.

It is also possible to incorporate beam splitter 22 as a polarized beam splitter. If so incorporated, a quarter wave plate 108 must be positioned on optical axis 18 somewhere between the polarized beam splitter 22 and cornea 38. Preferably, quarter wave plate 108 is positioned between beam splitter 30 and objective lens 32 as shown in FIG. 1. As so positioned, quarter wave plate 108 will effectively rotate the light in beam 12 in a manner well known to the skilled artisan so that reflected wave front 58 is diverted off optical axis 18 and toward lens array 64 by the polarized beam splitter 22.

As can be appreciated by reference to FIG. 1, the device of the present invention is adaptable for use with a surgical laser system 110. Specifically, a surgical laser system 110 can be optically positioned relative to beam splitter 30 to direct a laser cutting beam 112 toward cornea 38, in a manner well known in the art, for the purpose of performing ophthalmic surgery.

While the particular device for mapping corneal topography as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

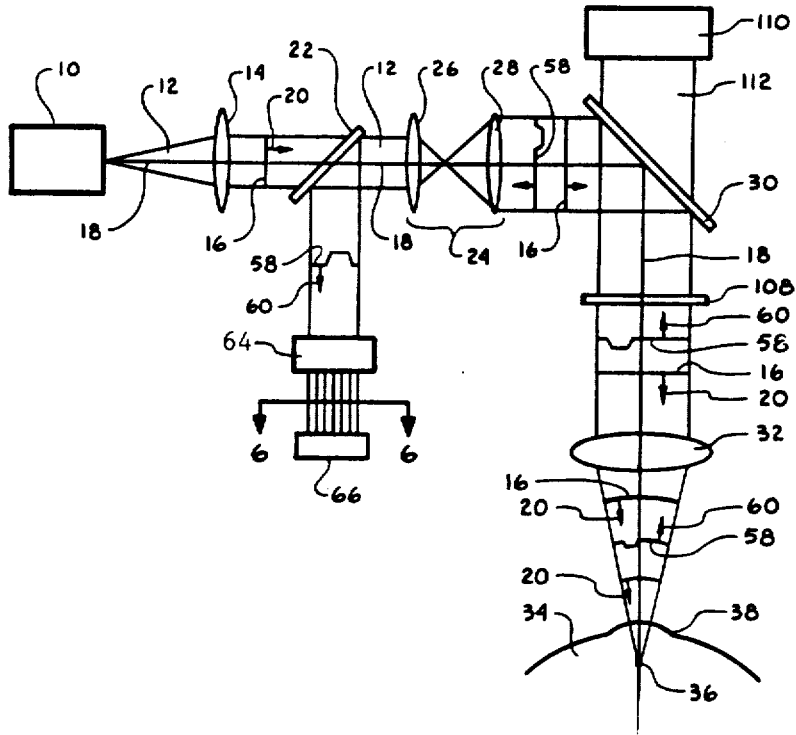

I claim:

1. A device for mapping the topography of the cornea of an eye which comprises:

means for generating a beam of collimated monochromatic light characterized by having a flat directed wave front;

means for directing said beam toward said cornea;

an objective lens for converting said flat wave front into a spherically converging wave front for incidence on said cornea;

means for receiving light of said beam reflected by said cornea, said reflected light being characterized by a reflected wave front indicative of said topography;

a charge-coupled device;

a lens array comprising a first layer having a plurality of juxtaposed cylindrical lenses and a second layer having a plurality of juxtaposed cylindrical lenses, said first layer being adjacent said second layer and substantially perpendicular thereto to collectively receive said reflected wave front to detect deviations of said reflected wave front from said flat wave front and individually focus the light incident on each of said cylindrical lenses onto said charge-coupled device to create a pattern on said charge-coupled device indicated of said topography.

2. A device for mapping the topography of the cornea of an eye which comprises:

a source for directing a beam of collimated monochromatic light along an optical axis, said optical axis extending between said source and said cornea, said beam being characterized by a flat directed wave front;

an objective lens for converting said flat wave front into a spherically converging wave front for incidence on said cornea;

a beam splitter positioned on said optical axis for diverting the light rays reflected by said cornea off said optical axis, said reflected light being characterized by a reflected wave front having deviations from said flat wave front indicative of said topography;

a detector having a lens array with a first layer having a plurality of juxtaposed cylindrical lenses and a second layer having a plurality of juxtaposed cylindrical lenses, said first layer being adjacent said second layer and substantially perpendicular thereto; and a charge-coupled device, said lens array being positioned to focus light onto said charge-coupled device to create a pattern thereon indicative of said topography.

3. A device as recited in claim 1 further comprising a polarized beam splitter for directing said reflected wave front toward said lens array and a quarter wave plate, said polarized beam splitter being positioned on said beam between said objective lens and beam generating means and said quarter wave plate being positioned on said beam between said objective lens and said polarized beam splitter.

4. A device as recited in claim 1 further comprising a polarized beam splitter for directing said reflected wave front toward said lens array and a quarter wave plate, said polarized beam splitter being positioned on said beam between said objective lens and beam generating means and said quarter wave plate being positioned on said beam between said objective lens and said polarized beam splitter.

5. A device as recited in claim 2 further comprising a polarized beam splitter for directing said reflected wave front toward said lens array and a quarter wave plate, said polarized beam splitter being positioned on said beam between said objective lens and beam generating means and said quarter wave plate being positioned on said beam between said objective lens and said polarized beam splitter.

* * * * *

UNITED STATES PATENT AND TRADEMARK OFFICE
CERTIFICATE OF CORRECTION

PATENT NO. : 5,062,702

DATED : November 5, 1991

INVENTOR(S) : Josef F. Bille

It is certified that error appears in the above-identified patent and that said Letters Patent is hereby corrected as shown below:

The title page, showing the illustrative figure should be deleted and therefor be replaced with the attached title page.

In the drawings, Figure 1, should be deleted and replaced with the corrected figure as shown on the attached page.

Signed and Sealed this

Second Day of March, 1993

Attest:

STEPHEN G. KUNIN

Attesting Officer

Acting Commissioner of Patents and Trademarks

United States Patent [19]

Bille

[11] Patent Number: 5,062,702
[45] Date of Patent: Nov. 5, 1991

[54] DEVICE FOR MAPPING CORNEAL TOPOGRAPHY

[75] Inventor: Josef F. Bille, Rancho Santa Fe, Calif.

[73] Assignee: Intelligent Surgical Lasers, Inc., San Diego, Calif.

[21] Appl. No.: 494,683

[22] Filed: Mar. 16, 1990

[51] Int. Cl.$^5$ .............................................. A61B 3/10
[52] U.S. Cl. ....................................... 351/212; 351/221
[58] Field of Search ....................... 351/206, 212, 221; 356/376

[56] References Cited

PUBLICATIONS

Ronald Cubalchini, Modal Wave-Front Estimation from Phase Derivative Measurements.
W. H. Southwell, Wave-Front Estimation from Wave-Front Slope Measurements, Optical Society of America, vol. 70, No. 8, Aug. 1980, pp. 998–1005.
H. C. Howland, Objective Technique for the Determination of Monochromatic Aberrations of the Human Eye, Optical Society of America, vol. 1, No. 9, Sep. 1984, pp. 987–992.
Klaus R. Freischlad and Chris L. Koliopoulos, Modal Estimation of a Wave Front from Difference Measurements Using the Discrete Fourier Transform, Optical Society of America, vol. 3, No. 11, Nov. 1986, pp. 1852–1861.
Stephen D. Klyce and Steven E. Wilson, Imaging, Reconstruction, and Display of Corneal Topography, New Methods in Microscopy and Low Light Imaging, vol. 1161, 1989, pp. 409–416.
J. F. Bille, B. Grimm, J. Liang, K. Mueller, Imaging of the Retina by Scanning Laser Tomography New Methods in Microscopy and Low Light Imaging, vol. 1161, 1989, pp. 417–425.
Phillip C. Baker, Holographic Contour Analysis of the Cornea, New Methods in Microscopy and Low Light Imaging, vol. 1161, 1989, pp. 426–437.
Modal Wave-Front Estimation from Phase Derivative Measurements.

Primary Examiner—Paul M. Dzierzynski
Attorney, Agent, or Firm—Nydegger Associates

[57] ABSTRACT

A device for mapping the topography of the cornea of an eye has a light source for directing a beam of collimated monochromatic light characterized by a flat wave front onto the cornea. Positioned between the light source and the cornea is an objective lens for focusing this flat wave front toward the cornea as a converging spherical wave front. The light reflected from the cornea passes back through the objective lens to establish a reflected wave front having deviations from the flat wave front caused by aberrations on the cornea that are indicative of corneal topography. This reflected wave front is then segmentally focused by a lens array into a pattern which reveals the deviations for use in mapping the topography of the cornea.

5 Claims, 2 Drawing Sheets